(12) United States Patent
Dunn et al.

(10) Patent No.: US 6,653,339 B2
(45) Date of Patent: Nov. 25, 2003

(54) METHOD OF TREATING IRRITABLE BOWEL SYNDROME

(75) Inventors: Peter James Dunn, Sandwich (GB); Michael John Humphrey, Sandwich (GB); Paul Quinn, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/218,735

(22) Filed: Aug. 13, 2002

(65) Prior Publication Data

US 2003/0114356 A1 Jun. 19, 2003

Related U.S. Application Data

(60) Provisional application No. 60/315,554, filed on Aug. 28, 2001.

(30) Foreign Application Priority Data

Aug. 15, 2001 (GB) .............................................. 0119919

(51) Int. Cl.⁷ .................................................. A61K 9/14
(52) U.S. Cl. ........................ 514/422; 514/960; 514/962
(58) Field of Search ................................ 514/422, 960, 514/962

(56) References Cited

U.S. PATENT DOCUMENTS

| 5,096,890 A | 3/1992 | Cross et al. ................. 514/422 |
| 6,106,864 A | 8/2000 | Dolan et al. ................. 424/488 |

FOREIGN PATENT DOCUMENTS

| WO | 9111172 | 8/1991 | ............ A61K/9/00 |
| WO | 9402518 | 2/1994 | ............ C08B/37/16 |
| WO | 9855148 | 12/1998 | ............ A61K/47/48 |

*Primary Examiner*—Frederick Krass
(74) *Attorney, Agent, or Firm*—Peter C. Richardson; Gregg C. Benson; Carl J. Goddard

(57) ABSTRACT

The present invention is directed to a a method for the treatment of irritable bowel syndrome comprising the multiple daily pulse dosing of an immediate release formulation of the anti-muscarinic darifenacin. Dosing two or three times a day is particularly preferred.

16 Claims, 1 Drawing Sheet

METHOD OF TREATING IRRITABLE BOWEL SYNDROME

This application claims priority from United Kingdom provisional application 0119919.9 filed on Aug. 15, 2001, and U.S. provisional application 60/315,554 filed Aug. 28, 2001.

FIELD OF THE INVENTION

The present invention is concerned with a method for the treatment of irritable bowel syndrome which involves the multiple daily dosing of an immediate release formulation of the anti-muscarinic darifenacin. Dosing two or three times a day is particularly preferred.

BACKGROUND OF THE INVENTION

Darifenacin is a muscarinic antagonist whose preparation and proposed use in the treatment of diseases associated with altered motility and/or tone of smooth muscle as found, for example, in the gut, trachea and bladder are described in U.S. Pat. No. 5,096,890. Specific diseases referred to include irritable bowel syndrome, diverticular disease, urinary incontinence, oesophageal achalasia and chronic obstructive airways disease. Of these, irritable bowel syndrome and urinary incontinence are particularly attractive targets for a muscarinic antagonist and controlled release formulations of darifenacin intended for use in the treatment of these diseases wherein at least 10% by weight of the darifenacin is released in the lower gastrointestinal tract are the subject of U.S. Pat. No. 6,106,864.

The text of these patents and all other references cited in this specification are hereby incorporated by reference in their entirety.

SUMMARY OF THE INVENTION

In one aspect, the invention is directed to a method for treating irritable bowel syndrome comprising a multiple daily pulse dosing of a darifenacin immediate release dosage form.

In a preferred embodiment, the immediate release dosage form is administered three times a day.

In another preferred embodiment, the immediate release dosage form is administered at about 8-hourly intervals.

In an other preferred embodiment, the immediate release dosage form is administered two times a day.

In a further preferred embodiment, the dosage form is administered at about 12-hourly intervals.

In an other preferred embodiment, the the immediate dosage form is administered prior to eating.

In a preferred embodiment, the dosage form is an immediate release tablet, capsule, liquid, or fast-dispersing or fast-dissolving dosage form or a form suitable for nasal or inhaled administration.

In a further preferred embodiment, the dosage form is an immediate release tablet or capsule.

In a preferred embodiment, the tablet or capsule contains approximately 2.5 mg of darifenacin.

In a preferred embodiment, the method is used for the treatment of constipated patients.

In an other preferred embodiment, the tablet or capsule contains approximately 5.0 mg or approximately 7.5 mg of darifenacin.

In a preferred embodiment, the method is used for the treatment of diarrhoea-predominant patients.

In a preferred embodiment, the plasma concentration of darifenacin exceeds that obtainable by controlled release medication at least twice a day.

In an other preferred embodiment, the plasma concentration of darifenacin exceeds that obtainable by controlled release medication three times a day.

In an other preferred embodiment, the plasma concentration of darifenacin exceeds that obtainable by controlled release medication twice a day.

In a preferred embodiment, the plasma concentration of darifenacin declines to less than 50% of its maximum value after 4 hours.

Figure 1:
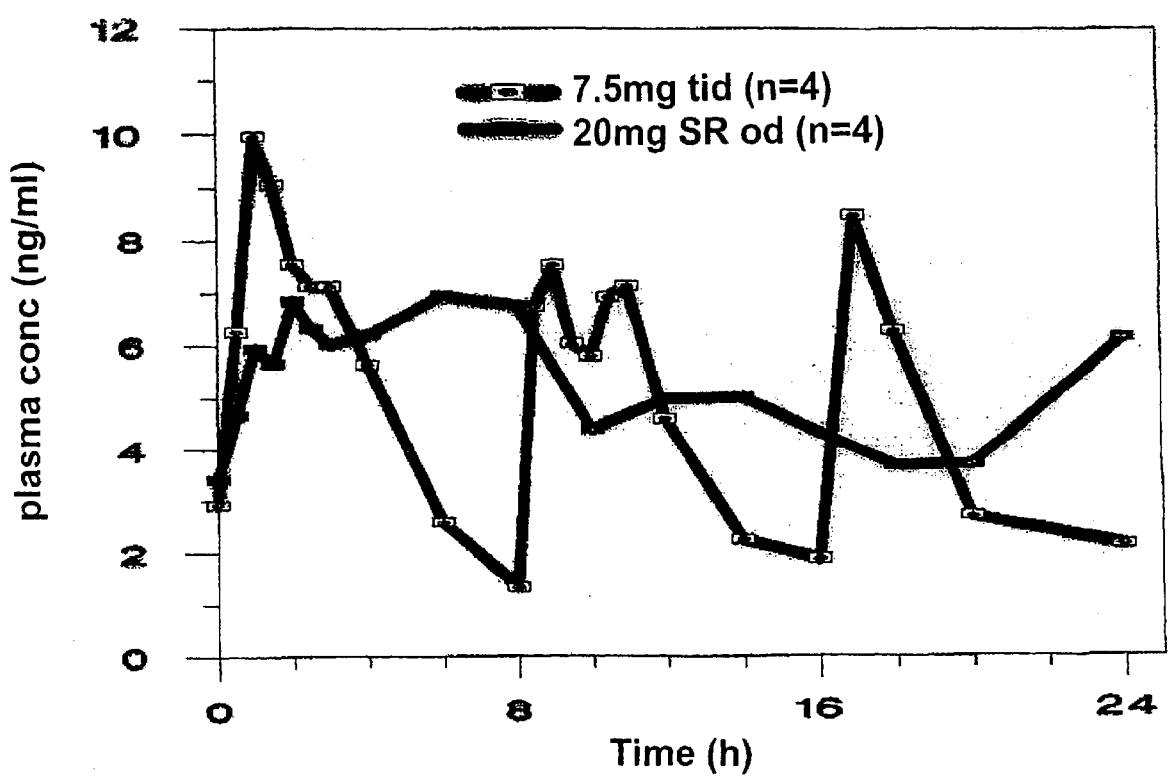
FIG. 1 shows the Day 6 plasma concentrations of darifenacin (ng/mL) in healthy volunteers following (i) a single oral dose of drug (20 mg SR od) for six days as a controlled (slow) release matrix tablet in accordance with the prior art and (ii) following multiple doses of drug (7.5 mg tid) for six days as a capsule in accordance with the present invention.

The data was obtained using an open, randomised, four-way crossover study in healthy male subjects. The subjects received each of the treatments for six days; these treatments ran continuously without a washout between study periods. Each subject received the drug either as a controlled (slow) release matrix tablet once daily (20 mg SR od) or as an immediate release capsule three times daily (7.5 mg tid). Plasma samples were taken at regular intervals throughout Day 6 of each study period from an indwelling catheter in the forearm. The samples were analyzed for darifenacin by high pressure liquid chromatogoraphy ("hplc")/mass spectrometry using calibration standards covering the concentration range 0.025 ng/mL to 2.0 ng/mL.

DETAILED DESCRIPTION OF THE INVENTION

For the treatment of irritable bowel syndrome, the Applicants considered the possibility of using a formulation or regime capable of sustaining a high dose of darifenacin in the upper rather than the lower gastrointestinal tract. The rapid absorption associated with this region would give rise to higher concentrations of darifenacin both locally and in the systemic circulation which might improve the efficacy of treating irritable bowel syndrome while not increasing the number of adverse events. High dosing in the upper gastrointestinal tract could be achieved, for example, by using a dosage form capable of delivering multiple doses of darifenacin during its passage through the stomach/duodenum or, more simply, by multiple dosing of an immediate release dosage form.

The Applicants have accordingly determined that multiple dosing of darifenacin immediate release dosage forms, for example, tablets or capsules, produces a significant improvement in the treatment of irritable bowel syndrome compared with the results obtained using the controlled release formulations of U.S. Pat. No. 6,106,864. In particular, multiple daily pulse dosing surprisingly improves efficacy while not increasing the number of adverse events.

The present invention, therefore, provides a method for treating irritable bowel syndrome with darifenacin which has improved efficacy over once-daily administration of the controlled release formulations of U.S. Pat. No. 6,106,864, while not increasing the number of adverse events.

The method of the present invention is found to be particularly advantageous when the immediate release dosage form of darifenacin is administered two times daily ("bid") at about 12-hourly intervals or three times daily ("tid") at about 8-hourly intervals. Administration before meals is preferred.

The surprising and advantageous results obtained using the method of the invention appear to result from periodic 'peaking' of the darifenacin plasma concentration above that of the controlled release curve (FIG. 1). According to a further aspect of the invention, the plasma concentration of darifenacin should exceed that obtainable by controlled release medication at least twice a day, preferably twice a day (bid) or three times a day (tid).

The rapid fall-off in plasma concentration of darifenacin after each dose is thought to reduce or prevent the development of tolerance towards the effects of the drug. According to yet another aspect of the invention, the plasma concentration of darifenacin should decline to less than 50% of its maximum value within 4 hours.

According to the present invention, there is provided a method for the treatment of irritable bowel syndrome which comprises the multiple daily pulse dosing of a darifenacin immediate release dosage form. The dosage form is preferably administered twice daily at intervals of about twelve hours or thrice daily at intervals of about eight hours. The latter regime is particularly preferred. Administration before meals is also preferred.

As used herein, the term "multiple daily dosing" is defined as dosing two or more times a day.

As used herein, the term "about" in the context of the hourly interval between dosing is defined as from two hours' earlier than the allotted time up to two hours later than the allotted time, preferably from one hour beforehand to one hour afterwards and most preferably from half an hour beforehand to half an hour afterwards.

As used herein, the term "administration before meals/prior to eating" is defined as dosing not more than two hours before a meal, preferably not more than an hour and a half before a meal and most preferably not more than one hour and not less than half an hour before a meal.

The darifenacin may be administered alone, but will generally be administered in admixture with a suitable pharmaceutical excipient, diluent, or carrier selected with regard to the intended route of administration and standard pharmaceutical practice. The immediate release dosage form will typically be a tablet, capsule, liquid (solution, suspension, etc.), or fast-dispersing or fast-dissolving dosage form, or a form suitable for nasal or inhaled administration.

The darifenacin may be administered, for example, orally, buccally, or sublingually in the form of tablets, capsules, multi-particulates, gels, films, ovules, elixirs, solutions, or suspensions. The darifenacin may also be administered as a fast-dispersing or fast-dissolving dosage form (see, for example, 'Fast-dissolving intraoral drug delivery systems' by Liang & Chen, *Expert Opin. Ther. Patents* (2001) 11 (6):981–986) or as an oral spray formulation. It may also be in the form of a high energy dispersion or as coated particles. Suitable formulations of darifenacin may be in coated or uncoated form, as desired.

The 2.5 mg immediate release dosage form has been found particularly satisfactory for the purposes of the invention, though for patients having poor absorption a higher dosage form may be preferred. Thus a 2.5 mg tablet or capsule may be suitable for constipated patients, while a 5.0 mg or 7.5 mg tablet or capsule may be preferred for diarrhoea-predominant patients.

Such solid pharmaceutical compositions, for example, tablets, may contain excipients such as microcrystalline cellulose, lactose, sodium citrate, calcium carbonate, dibasic calcium phosphate, glycine and starch (preferably corn, potato, or tapioca starch), disintegrants such as sodium starch glycollate, croscarmellose sodium and certain complex silicates, granulation binders such as polyvinylpyrrolidone, hydroxypropylmethylcellulose (HPMC), hydroxypropylcellulose (HPC), sucrose, gelatin and acacia, and flavouring and/or colouring agents. Additionally, lubricating agents such as magnesium stearate, stearic acid, glyceryl behenate and talc may be included.

A tablet formulation for use in accordance with the present invention would typically contain from about 0.5 mg to about 10 mg of darifenacin, whilst tablet fill weights may range from 50 mg to 1000 mg. Tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar, or high molecular weight polyethylene glycols. Again, capsules would typically contain from about 0.5 mg to about 10 mg of darifenacin. Details of immediate release capsule formulations suitable for use in the present invention are to be found in the clinical studies.

For aqueous suspensions and/or elixirs, the darifenacin may be combined with various sweetening or flavouring agents, colouring matter or dyes, with emulsifying and/or suspending agents and with diluents such as water, ethanol, propylene glycol and glycerin, and combinations thereof.

As indicated, tablets or capsules for use in accordance with the invention may contain from about 0.5 mg to about 10 mg of darifenacin for administration as single doses at appropriate intervals throughout the day. The overall daily dose by oral administration will usually be from about 1.5 mg to about 30 mg. A typical daily dose would be three 5 mg tablets or capsules administered at approximately 8-hourly intervals. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The darifenacin can also be administered intranasally or by inhalation and is conveniently delivered in the form of a dry powder inhaler or insufflator or an aerosol spray presentation from a pressurised container, pump, spray, atomiser, or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A®) or 1,1,1,2,3,3,3-heptafluoropropane (HFA 227EA®), carbon dioxide or other suitable gas. In the case of a pressurised aerosol, the dosage unit may be determined by providing a valve to deliver a metered amount. The pressurised container, pump, spray, atomiser, or nebuliser may contain a solution or suspension of darifenacin, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of darifenacin and a suitable powder base such as lactose or starch.

Aerosol or dry powder formulations are preferably arranged so that each metered dose or "puff" contains from 0.2 mg to 3.0 mg of darifenacin for administration in single doses at appropriate intervals throughout the day. The overall daily dose by aerosol administration will usually be from 0.5 mg to 10 mg. A typical daily dose would be three 2.0 mg metered doses administered at approximately 8-hourly intervals.

The darifenacin may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the darifenacin, the cyclodextrin may be used as an auxiliary additive, e.g. as a carrier, diluent, or solubilizer. Alpha-, beta- and gamma-cyclodextrins are most commonly used and suitable examples are described in published International Patent Applications WO-A-91/1 1172, WO-A-94/02518 and WO-A-98/55148.

Clinical Studies

The invention may be illustrated by the following clinical studies wherein the treatment of irritable bowel syndrome using darifenacin administered as a once-daily controlled (slow) release formulation in accordance with the prior art is compared with treatment using darifenacin administered as a thrice daily immediate release formulation in accordance with the present invention. Specifically, Clinical Studies 1 and 2 used controlled (slow) release formulations of darifenacin administered once daily (od) and Clinical Study 3 used an immediate release formulation of darifenacin administered three times daily (tid).

During each clinical study, four efficacy measures of irritable bowel syndrome severity were measured, viz. 'Pain Score' (Average daily pain score, a composite of severity and number of days of pain), 'Loose Stool' (Number of days on which loose or watery stool occurred), 'Urgency' (Number of days on which urgency occured) and so-called 'Global Rating' (Patient rating of their condition taking into account all symptoms, 0=no problems). Adverse events (AE) such as constipation, dry mouth and visual abnormalities were also recorded.

Clinical Studies 1 and 2 (Comparative)

Clinical Study 1 was a multi-centre, double-blind, randomised, placebo-controlled parallel group study in which three dose strengths of darifenacin of 3.75 mg, 7.5 mg and 15 mg dosed od were compared with placebo. Treatment lasted 12 weeks following a 2-week run-in period.

Clinical Study 2 was a multi-centre, double-blind, randomised, placebo-controlled parallel group study in which four dose strengths of darifenacin of 3.75 mg, 7.5 mg, 15 mg and 30 mg dosed od were compared with placebo. Treatment lasted 12 weeks following a 2-week run-in period.

The controlled (slow) release dosage forms of darifenacin used in Clinical Studies 1 and 2 were 3.75 mg, 7.5 mg, 15.0 mg and 30.0 mg tablets having the following compositions:

TABLE 1

Slow Release Dosage Forms of Darifenacin

| Ingredient | By weight (3.75 mg) | By weight (7.5 mg) | By weight (15.0 mg) | By weight (30.0 mg) |
|---|---|---|---|---|
| Darifenacin hydrobromide | 4.46 | 8.93 | 17.86 | 35.71 |
| Methylhydroxy propyl cellulose | 114.40 | 114.40 | 114.40 | 114.40 |
| Calcium phosphate dibasic (anhydrous) | 79.14 | 74.67 | 65.74 | 47.89 |
| Magnesium stearate | 2.00 | 2.00 | 2.00 | 2.00 |
| Opadry film coat | Approx 2.5% | Approx 2.5% | Approx 2.5% | Approx 2.5% |
| Total weight | 200 mg + film coat | 200 mg + film coat | 200 mg + film coat | 200 mg + fillm coat |

Clinical Study 3

Clinical Study 3 was a multi-centre, double-blind, randomised, placebo-controlled parallel group study in which three dose strengths of darifenacin 1.25, 2.5 and 5 mg dosed tid were compared with placebo. Treatment lasted 12 weeks following a 2-week run-in period.

The immediate release dosage forms of darifenacin used in Clinical Study 3 were 1.25 mg, 2.5 mg and 5.0 mg capsules having the following compositions in a Size 3 capsule shell:

TABLE 2

Immediate Release Dosage Forms of Darifenacin

| Ingredient | By weight (mg) (1.25 mg) | By weight (mg) (2.5 mg) | By weight (mg) (5.0 mg) |
|---|---|---|---|
| Darifenacin hydrobromide | 1.49 | 2.98 | 5.95 |
| Lactose | 110.03 | 108.92 | 106.69 |
| Maize starch | 36.68 | 36.31 | 35.56 |
| Colloidal anhydrous silica | 0.30 | 0.30 | 0.30 |
| Magnesium stearate | 1.50 | 1.50 | 1.50 |
| Total content | 150.0 mg | 150.0 mg | 150.0 mg |

The immediate release dosage form may also be in the form of a tablet analogous to that described for the controlled (slow) release dosage form (vide supra) wherein the methylhydroxy propyl cellulose is replaced by microcrystalline cellulose (Avicel PH102).

Results

CLINICAL STUDY 1 - CONTROLLED
RELEASE (OD) - COMPARATIVE

TABLE 3

| | Uncorrected Data | | | |
|---|---|---|---|---|
| | Placebo | 3.75 mg | 7.5 mg | 15 mg |
| | % Reduction from baseline | | | |
| Pain Score | 38 | 35 | 43 | 39 |
| Loose Stool | 33 | 37 | 37 | 47 |
| Urgency | 23 | 41 | 40 | 50 |
| Global Rating | 29 | 27 | 29 | 31 |

TABLE 3-continued

Uncorrected Data

| | Placebo | 3.75 mg | 7.5 mg | 15 mg |
|---|---|---|---|---|
| % of patients reporting AEs | | | | |
| Constipation | 5.8 | 7.2 | 10.5 | 15.2 |
| Dry Mouth | 7.7 | 10.2 | 14.2 | 28.5 |
| Vision | 1.9 | 5.4 | 4.3 | 3.3 |
| Total AE | 25 | 27 | 28 | 40 |

TABLE 4

Placebo-corrected Data

| | 3.75 mg | 7.5 mg | 15 mg |
|---|---|---|---|
| % Reduction from baseline corrected for placebo | | | |
| Pain Score | −3 | 5 | 1 |
| Loose Stool | 4 | 4 | 14 |
| Urgency | 18 | 17 | 27 |
| Global Rating | −2 | 0 | 2 |
| % of patients reporting AEs corrected for placebo | | | |
| Constipation | 1.4 | 4.7 | 9.4 |
| Dry Mouth | 2.5 | 6.5 | 20.8 |
| Vision | 5.4 | 4.3 | 3.3 |
| Total AE | 2 | 3 | 15 |

CLINICAL STUDY 2 - CONTROLLED RELEASE (OD) - COMPARATIVE

TABLE 5

Uncorrected Data

| | Placebo | 3.75 mg | 7.5 mg | 15 mg | 30 mg |
|---|---|---|---|---|---|
| % Reduction from basetine | | | | | |
| Pain Score | 37 | 28 | 37 | 39 | 40 |
| Loose Stool | 23 | 31 | 39 | 53 | 50 |
| Urgency | 25 | 24 | 33 | 47 | 41 |
| Global Rating | 28 | 21 | 27 | 32 | 36 |
| % of patients reporting AEs | | | | | |
| Constipation | 1.9 | 6.4 | 7.8 | 13.5 | 17 |
| Dry Mouth | 5.2 | 9.6 | 9.6 | 25 | 35.9 |
| Vision | 0.6 | 1.3 | 1.2 | 3.2 | 5.2 |
| Total AE | 16 | 22 | 22 | 41 | 50 |

TABLE 6

Placebo-corrected Data

| | 3.75 mg | 7.5 mg | 15 mg | 30 mg |
|---|---|---|---|---|
| % Reduction from baseline corrected for placebo | | | | |
| Pain Score | −9 | 0 | 2 | 3 |
| Loose Stool | 8 | 16 | 30 | 27 |
| Urgency | −1 | 8 | 22 | 26 |
| Global Rating | −7 | −1 | 4 | 8 |
| % of patients reporting AEs corrected for placebo | | | | |
| Constipation | 4.5 | 5.9 | 11.6 | 15.1 |
| Dry Mouth | 4.4 | 4.4 | 19.8 | 30.7 |
| Vision | 0.7 | 0.6 | 2.6 | 4.6 |
| Total AE | 6 | 6 | 15 | 34 |

It can be seen from both controlled release od studies that, while the higher doses gave improvements in the efficacy measures of Loose Stool and Urgency, no effects were seen on the key measures of Pain Score and Global Rating. In addition, the number of adverse effects showed a marked increase with dose.

CLINICAL STUDY 3 - IMMEDIATE RELEASE (TID)

TABLE 7

Uncorrected Data

| | Placebo | 3 × 1.25 mg | 3 × 2.5 mg | 3 × 5.0 mg |
|---|---|---|---|---|
| % Reduction from baseline | | | | |
| Pain Score | 23 | 33 | 40 | 36 |
| Loose Stool | 8 | 16 | 30 | 52 |
| Urgency | 25 | 36 | 42 | 57 |
| Global Rating | 18 | 27 | 29 | 32 |
| % of patients reporting AEs | | | | |
| Constipation | 2.9 | 6.3 | 5.6 | 11.3 |
| Dry Mouth | 15.7 | 16 | 24.5 | 49.6 |
| Vision | 3.6 | 1.4 | 3.5 | 7.8 |
| Total AE | 40 | 36 | 37 | 60 |

TABLE 8

Placebo-corrected Data

| | 3 × 1.25 mg | 3 × 2.5 mg | 3 × 5.0 mg |
|---|---|---|---|
| % Reduction from baseline corrected for placebo | | | |
| Pain Score | 10 | 17 | 13 |
| Loose Stool | 8 | 22 | 44 |
| Urgency | 11 | 17 | 32 |
| Global Rating | 9 | 11 | 14 |
| % of patients reporting AEs corrected for placebo | | | |
| Constipation | 3.4 | 5.6 | 8.4 |
| Dry Mouth | 0.3 | 8.8 | 33.9 |
| Vision | −2.2 | −0.1 | 4.2 |
| Total AE | −4 | −3 | 20 |

It can be seen from the immediate release tid study that all three doses gave marked improvements in all four efficacy measures (Pain Score, Loose Stool, Urgency and Global Rating); the number of adverse events were similar to those seen with controlled (slow) release.

What is claimed is:

1. A method for treating irritable bowel syndrome comprising administering a multiple daily pulse dosing of a darifenacin immediate release dosage form to a subject in need of said treatment.

2. A method according to claim 1 wherein the immediate release dosage form is administered three times a day.

3. A method according to claim 2, wherein the immediate release dosage form is administered at about 8-hourly intervals.

4. A method according to claim 1, wherein the immediate release dosage form is administered two times a day.

5. A method according to claim 4, wherein the dosage form is administered at about 12-hourly intervals.

6. A method according to claim 1, wherein the immediate dosage form is administered prior to eating.

7. A method according to any of claims 1, 2, 3, 4, 5, or 6 wherein the dosage form is an immediate release tablet, capsule, liquid, or fast-dispersing or fast-dissolving dosage form or a form suitable for nasal or inhaled administration.

8. A method according to claim 7 wherein said dosage form is an immediate release tablet or capsule.

9. A method according to claim 8 wherein said tablet or capsule contains approximately 2.5 mg of darifenacin.

10. A method according to claim 9 for the treatment of constipated patients.

11. A method according to claim 8 wherein said tablet or capsule contains approximately 5.0 mg or approximately 7.5 mg of darifenacin.

12. A method according to claim 11 for the treatment of diarrhoea-predominant patients.

13. A method according to any of claims 1, 2, 3, 4, 5, or 6, wherein the plasma concentration of darifenacin exceeds that obtainable by administering a controlled release medication at least twice a day.

14. A method according to claim 13, wherein the plasma concentration of darifenacin exceeds that obtainable by administering a controlled release medication three times a day.

15. A method according to claim 13 wherein the plasma concentration of darifenacin exceeds that obtainable by administering a controlled release medication twice a day.

16. A method according to any of claims 1, 2, 3, 4, 5 or 6, wherein the plasma concentration of darifenacin declines to less than 50% of its maximum value after 4 hours.

* * * * *